(12) United States Patent
Ivancich et al.

(10) Patent No.: US 11,222,712 B2
(45) Date of Patent: Jan. 11, 2022

(54) PRIMER DESIGN USING INDEXED GENOMIC INFORMATION

(71) Applicant: NOBLIS, INC., Reston, VA (US)

(72) Inventors: Mychal W. Ivancich, Reston, VA (US); Danielle E. Montoya, Woodbridge, VA (US)

(73) Assignee: NOBLIS, INC., Reston, VA (US)

( * ) Notice: Subject to any disclaimer, the term of this patent is extended or adjusted under 35 U.S.C. 154(b) by 806 days.

(21) Appl. No.: 15/977,659

(22) Filed: May 11, 2018

(65) Prior Publication Data

US 2018/0330053 A1    Nov. 15, 2018

Related U.S. Application Data

(60) Provisional application No. 62/505,409, filed on May 12, 2017.

(51) Int. Cl.
| | | |
|---|---|---|
| *G16B 25/20* | (2019.01) | |
| *C12Q 1/6853* | (2018.01) | |
| *G16B 30/00* | (2019.01) | |
| *G16B 50/00* | (2019.01) | |
| *G16B 20/00* | (2019.01) | |
| *C12Q 1/6811* | (2018.01) | |
| *G16B 20/30* | (2019.01) | |
| *G16B 50/10* | (2019.01) | |
| *G16B 50/50* | (2019.01) | |
| *G16B 50/30* | (2019.01) | |

(52) U.S. Cl.
CPC ............ *G16B 25/20* (2019.02); *C12Q 1/6811* (2013.01); *C12Q 1/6853* (2013.01); *G16B 20/00* (2019.02); *G16B 20/30* (2019.02); *G16B 30/00* (2019.02); *G16B 50/00* (2019.02); *G16B 50/10* (2019.02); *G16B 50/30* (2019.02); *G16B 50/50* (2019.02)

(58) Field of Classification Search
None
See application file for complete search history.

(56) References Cited

U.S. PATENT DOCUMENTS

| | | | |
|---|---|---|---|
| 5,994,068 | A | 11/1999 | Guilfoyle et al. |
| 6,141,657 | A | 10/2000 | Rothberg et al. |
| 6,280,948 | B1 | 8/2001 | Guilfoyle et al. |
| 8,209,130 | B1 | 6/2012 | Kennedy et al. |
| 8,812,243 | B2 | 8/2014 | Cardonha et al. |
| 2002/0058256 | A1 | 5/2002 | Rothberg et al. |
| 2004/0002816 | A1 | 1/2004 | Milosavljevic |
| 2004/0048264 | A1 | 3/2004 | Stoughton et al. |
| 2004/0053246 | A1 | 3/2004 | Sorenson |
| 2004/0224330 | A1 | 11/2004 | He |
| 2005/0049795 | A1 | 3/2005 | Fikuda |
| 2005/0107960 | A1 | 5/2005 | Toyoda |
| 2005/0239102 | A1 | 10/2005 | Verdine |
| 2006/0112264 | A1 | 5/2006 | Agarwal |
| 2006/0286566 | A1 | 12/2006 | Lapidus et al. |
| 2007/0016612 | A1 | 1/2007 | James et al. |
| 2008/0027656 | A1 | 1/2008 | Parida |
| 2008/0168572 | A1 | 7/2008 | Stetter et al. |
| 2009/0055425 | A1 | 2/2009 | Evans et al. |
| 2009/0233802 | A1 | 9/2009 | Bignell et al. |
| 2009/0270277 | A1 | 10/2009 | Glick et al. |
| 2009/0292665 | A1 | 11/2009 | Den Hartog |
| 2010/0114918 | A1 | 5/2010 | Karlsen |
| 2010/0287165 | A1 | 11/2010 | Halpern et al. |
| 2011/0103501 | A1 | 5/2011 | Khojastepour et al. |
| 2011/0257889 | A1 | 10/2011 | Klammer et al. |
| 2011/0264377 | A1 | 10/2011 | Cleary |
| 2011/0270533 | A1 | 11/2011 | Zhang |
| 2011/0295858 | A1 | 12/2011 | Ahn et al. |
| 2012/0016658 | A1 | 1/2012 | Wu et al. |
| 2012/0046877 | A1 | 2/2012 | Hyland |
| 2012/0296810 | A1 | 11/2012 | Bates |
| 2013/0203973 | A1 | 8/2013 | Wilkerson et al. |
| 2013/0268206 | A1 | 10/2013 | Porreca et al. |
| 2013/0304392 | A1 | 11/2013 | Deciu et al. |
| 2013/0338934 | A1 | 12/2013 | Asadi et al. |
| 2014/0075183 | A1 | 3/2014 | Wang et al. |

(Continued)

FOREIGN PATENT DOCUMENTS

| | | |
|---|---|---|
| CA | 2036946 | 10/2001 |
| CN | 102682226 | 9/2012 |

(Continued)

OTHER PUBLICATIONS

Thomas et al., U.S. Office Action dated Jan. 25, 2021, directed to U.S. Appl. No. 16/257,552; 21 pages.

Flicek et al. (Nov. 2009). "Sense from Sequence Reads: Methods for Alignment and Assembly," Nature Methods Supplement 6(11): 6-12; Corrigendum: 1.

Hancock-Hanser et al. (2013). "Targeted Multiplex Next-Generation Sequencing: Advances in Techniques of Mitochondrial and Nuclear DNA Sequencing for Population Genomics," Molecular Ecology Resources 13: 254-268.

(Continued)

*Primary Examiner* — John S Brusca
(74) *Attorney, Agent, or Firm* — Morrison & Foerster LLP

(57) ABSTRACT

Techniques for identifying regions in nucleic acid sequences for which to design highly discriminatory primers are provided. In some embodiments, a corpus of nucleic acid sequences may be divided into a first set and a second set, and a respective index may be built containing data structures representing a plurality of k-mers of each nucleic acid sequence. By comparing the data structures of the first index to one another, a system may iteratively determine whether each k-mer over a given region in one of the nucleic acid sequences in the first set are also found in every other sequence in the first set. By comparing against the data structures in the second index, a system may then iteratively determine whether all k-mers in the region can be found in the same order of in any of the nucleic acid sequences in the second set.

14 Claims, 4 Drawing Sheets

Specification includes a Sequence Listing.

(56) References Cited

U.S. PATENT DOCUMENTS

| | | | |
|---|---|---|---|
| 2014/0358937 A1 | 12/2014 | Thomas et al. |
| 2016/0306919 A1 | 10/2016 | Ding et al. |
| 2016/0344849 A1 | 11/2016 | Thomas et al. |
| 2019/0146962 A1 | 5/2019 | Thomas et al. |

FOREIGN PATENT DOCUMENTS

| | | |
|---|---|---|
| WO | 94/01582 | 1/1994 |
| WO | 01/098535 A2 | 12/2001 |
| WO | 2005/096208 A1 | 10/2005 |
| WO | 2007/137225 A2 | 11/2007 |
| WO | 2008/000090 A1 | 1/2008 |
| WO | 2010/104608 A2 | 9/2010 |
| WO | 2012/168815 A2 | 12/2012 |

OTHER PUBLICATIONS

International Search Report and Written Opinion dated Sep. 7, 2016, directed to International Application No. PCT/US2016/033786; 9 pages.

Li et al. (Jun. 1, 2009). "SNP Detection for Massively Parallel Whole-Genome Resequencing," Genome Research 19: 1124-1132.

Mehta et al. (2010). "DNA Compression Using Hash Based Data Structure," International Journal of Information Technology and Knowledge Management 2(2): 383-386.

Munoz-Torres et al. (2011). "Hymenoptera Genome Database: Integrated Community Resources for Insect Species of The Order Hymenoptera," Nucleic Acids Research 39(1): D658-D662.

Ning et al. (2011). "SSAHA: A Fast Search Method for Large DNA Databases," Genome Research 11: 1725-1729.

Office Action dated Oct. 19, 2017, directed to Chinese Application No. 201410228956.7; 10 pages.

Ossowski et al. (Oct. 3, 2008). "Sequencing of Natural Strains of *Arabidopsis thaliana* with Short Reads," Genome Research 18: 2024-2033.

Search Report dated May 7, 2015, directed to European Application No. 14170198.7, 17 pages.

Thomas et al., U.S. Office Action dated Nov. 27, 2017, directed to U.S. Appl. No. 14/718,950; 19 pages.

Thomas et al., U.S. Office Action dated Dec. 29, 2016, directed to U.S. Appl. No. 13/904,738; 23 pages.

Thomas et al., U.S. Office Action dated Jan. 28, 2015, directed to U.S. Appl. No. 13/904,738; 17 pages.

Thomas et al., U.S. Office Action dated Jun. 27, 2018, directed to U.S. Appl. No. 13/904,738; 32 pages.

Thomas et al., U.S. Office Action dated Mar. 24, 2016, directed to U.S. Appl. No. 13/904,738; 21 pages.

Thomas et al., U.S. Office Action dated May 24, 2017, directed to U.S. Appl. No. 14/718,950; 14 pages.

Thomas et al., U.S. Office Action dated May 28, 2015, directed to U.S. Appl. No. 13/904,738; 22 pages.

Thomas et al., U.S. Office Action dated Nov. 1, 2017, directed to U.S. Appl. No. 13/904,738; 24 pages.

Thomas et al., U.S. Office Action dated May 30, 2018, directed to U.S. Application No. 14/718,950, 21 pages.

Tsaftaris et al. (2007). "Retrieval Accuracy of Very Large DNA-Based Databases of Digital Signals," European Signal Processing Conference (EUSIPCO):1561-1565.

Thomas et al., Office Action dated Feb. 13, 2019, directed to U.S. Appl. No. 14/718,950; 12 pages.

Examination Report dated Dec. 12, 2019, directed to IN Application No. 1682/MUM/2014; 7 pages.

Thomas et al., U.S. Office Action dated Jul. 15, 2021, directed to U.S. Appl. No. 16/257,552; 24 pages.

200

206
...GTAAGATCCGCTACAA...ATCCGCTAATGCGCCGTAGTCCG...

202a

| 0 | AAAAAAAAAAAAAAAA |
| 1 | AAAAAAAAAAAAAAAT |
| 2 | AAAAAAAAAAAAAATA |
| 3 | AAAAAAAAAAAAAATT |

⋮

202b → 204a → 204b

| n | GTAAGATCCGCTACAA | → | 0 | → | 21 |
| n+1 | GTAAGATCCGCTACAT |
| n+2 | GTAAGATCCGCTACTA | → | 44 |

202c  204c

⋮

| $4^k-4$ | CGCCCCCCCCCCCCCG |
| $4^k-3$ | CGCCCCCCCCCCCCGC |
| $4^k-2$ | CGCCCCCCCCCCCCCC |
| $4^k-1$ | CCCCCCCCCCCCCCCC |

SEQUENCE LISTING

<160> NUMBER OF SEQ ID NOS: 14

<210> SEQ ID NO 1
<211> LENGTH: 16
<212> TYPE: DNA
<213> ORGANISM: Unknown
<220> FEATURE:
<223> OTHER INFORMATION: Exemplary construct

<400> SEQUENCE: 1
gtaagatccg ctacaa                    16

<210> SEQ ID NO 2
<211> LENGTH: 23
<212> TYPE: DNA
<213> ORGANISM: Unknown
<220> FEATURE:
<223> OTHER INFORMATION: Exemplary construct

<400> SEQUENCE: 2
atccgctaat gcgccgtagt ccg                23

```
<210> SEQ ID NO 3
<211> LENGTH: 16
<212> TYPE: DNA
<213> ORGANISM: Unknown
<220> FEATURE:
<223> OTHER INFORMATION: Exemplary construct

<400> SEQUENCE: 3
aaaaaaaaaa aaaaaa                                                      16

<210> SEQ ID NO 4
<211> LENGTH: 16
<212> TYPE: DNA
<213> ORGANISM: Unknown
<220> FEATURE:
<223> OTHER INFORMATION: Exemplary construct

<400> SEQUENCE: 4
aaaaaaaaaa aaaaat                                                      16

<210> SEQ ID NO 5
<211> LENGTH: 16
<212> TYPE: DNA
<213> ORGANISM: Unknown
<220> FEATURE:
<223> OTHER INFORMATION: Exemplary construct

<400> SEQUENCE: 5
aaaaaaaaaa aaaata                                                      16

<210> SEQ ID NO 6
<211> LENGTH: 16
<212> TYPE: DNA
<213> ORGANISM: Unknown
<220> FEATURE:
<223> OTHER INFORMATION: Exemplary construct

<400> SEQUENCE: 6
aaaaaaaaaa aaaatt                                                      16

<210> SEQ ID NO 7
<211> LENGTH: 16
<212> TYPE: DNA
<213> ORGANISM: Unknown
<220> FEATURE:
<223> OTHER INFORMATION: Exemplary construct

<400> SEQUENCE: 7
gtaagatccg ctacat                                                      16

<210> SEQ ID NO 8
<211> LENGTH: 16
<212> TYPE: DNA
<213> ORGANISM: Unknown
<220> FEATURE:
<223> OTHER INFORMATION: Exemplary construct

<400> SEQUENCE: 8
gtaagatccg ctacta                                                      16

<210> SEQ ID NO 9
<211> LENGTH: 16
<212> TYPE: DNA
<213> ORGANISM: Unknown
<220> FEATURE:
<223> OTHER INFORMATION: Exemplary construct
```

```
<400> SEQUENCE: 9
cgcccccccc ccccg                                                   16

<210> SEQ ID NO 10
<211> LENGTH: 16
<212> TYPE: DNA
<213> ORGANISM: Unknown
<220> FEATURE:
<223> OTHER INFORMATION: Exemplary construct

<400> SEQUENCE: 10
cgcccccccc ccccgc                                                  16

<210> SEQ ID NO 11
<211> LENGTH: 16
<212> TYPE: DNA
<213> ORGANISM: Unknown
<220> FEATURE:
<223> OTHER INFORMATION: Exemplary construct

<400> SEQUENCE: 11
cgcccccccc cccccc                                                  16

<210> SEQ ID NO 12
<211> LENGTH: 16
<212> TYPE: DNA
<213> ORGANISM: Unknown
<220> FEATURE:
<223> OTHER INFORMATION: Exemplary construct

<400> SEQUENCE: 12
cccccccccc cccccc                                                  16

<210> SEQ ID NO 13
<211> LENGTH: 16
<212> TYPE: DNA
<213> ORGANISM: Unknown
<220> FEATURE:
<223> OTHER INFORMATION: Exemplary construct

<400> SEQUENCE: 13
attgcttcca tgggtc                                                  16

<210> SEQ ID NO 14
<211> LENGTH: 108
<212> TYPE: PRT
<213> ORGANISM: Unknown
<220> FEATURE:
<223> OTHER INFORMATION: Exemplary construct

<400> SEQUENCE: 14

Asp Val Gln Met Ile Gln Ser Pro Ser Ser Leu Ser Ala Ser Leu Gly
 1               5                  10                  15

Asp Ile Val Thr Met Thr Cys Gln Ala Ser Gln Gly Thr Ser Ile Asn
                20                  25                  30

Leu Asn Trp Phe Gln Gln Lys Pro Gly Lys Ala Pro Lys Leu Leu Ile
            35                  40                  45

Tyr Gly Ser Ser Asn Leu Glu Asp Gly Val Pro Ser Arg Phe Ser Gly
        50                  55                  60

Ser Arg Tyr Gly Thr Asp Phe Thr Leu Thr Ile Ser Ser Leu Glu Asp
65                  70                  75                  80
```

-continued

```
Glu Asp Leu Ala Thr Tyr Phe Cys Leu Gln His Ser Tyr Leu Pro Tyr
                85                  90                  95
Thr Phe Gly Gly Gly Thr Lys Leu Glu Ile Lys Arg
            100                 105
```

PRIMER DESIGN USING INDEXED GENOMIC INFORMATION

REFERENCE TO RELATED APPLICATIONS

This application claims the benefit of U.S. Provisional Application No. 62/505,409, entitled, "PRIMER DESIGN USING INDEXED GENOMIC INFORMATION," filed May 12, 2017, the entire contents of which are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 739642003000SEQLIST, date recorded: Jul. 24, 2018, size: 4 KB).

FIELD OF THE INVENTION

This relates to systems and methods for storage and analysis of genomic information for the design of primers.

BACKGROUND OF THE INVENTION

Identification of bacterial organisms and viruses plays an important role in a multitude of areas such as healthcare, biodefense, research, and food safety. Continually increasing databases of sequence data has made it possible to identify regions specific to species, even serotypes of bacteria, as well as various classes of virus.

Rational design of new primers targeting highly discriminatory regions is essential for the effectiveness of diagnostic assays. Most existing species-specific assays were designed based on limited sequence information and were gene-specific due to historical or laboratory-specific influences. Designing primers in this way is time-intensive and labor-intensive, requires pre-existing knowledge about characteristics of the nucleic acid sequences for which the primers are to be designed, and may not be rapidly and automatically adaptable to account for new or additional genomic information in designing new primers or replacing old ones.

SUMMARY OF THE INVENTION

As explained above, known methods for primer design are time-intensive and labor-intensive and depend on historical and background knowledge of relevant genes and genomic characteristics. Accordingly, improved techniques for the rational design of new primers targeting highly discriminatory regions are needed, wherein the techniques allow for the rapid and computationally efficient determination of highly discriminatory regions for primer design. There is a need for such techniques that are easily adjustable to suit the needs of different applications, and that can quickly integrate new sequencing data as it becomes available.

Accordingly, disclosed herein are systems, methods, and techniques for rapid and computationally efficient determination of highly discriminatory regions for primer design.

In some embodiments, primer design may be achieved by creating an index comprised of all available reference genomes and enabling an exhaustive comparison approach by executing a brute force search method. One organism, either a reference genome or a read set, may then be compared to all other references available within an index to determine unique k-mers. These k-mers comprise signature sequences for a desired target derived from whole genome sequencing data and can be used to design new primers for PCR-based identification in silico. This approach may extract signature sequences by simultaneously comparing all possible k-mers generated from a chosen target genome with all available reference genomes from which it would be desirable to generate distinct primers. From this one-to-many comparison, a set of candidate signature sequence regions may be identified. These regions can then be used to design primers with high specificity.

In some embodiments, a method for identifying a region for which to design one or more primers for nucleic acid sequences is provided, the method comprising: at a system comprising one or more processors and memory storing instructions executable by the processor: receiving genomic data representing a plurality of nucleic acid sequences; creating and storing data in a first index representing a first set of the plurality of nucleic acid sequences; creating and storing data in a second index representing a second set of the plurality of nucleic acid sequences; identifying a region for which to design a primer that selects for one or more of the nucleic acid sequences in the first set and that discriminates against one or more of the nucleic acid sequences in the second set, wherein the identifying comprises: identifying, by the first index, the region as a region appearing in every nucleic acid sequence in the first set; and confirming, by the second index, that the region appears in none of the nucleic acid sequences in the second set; and generating and outputting data representing a primer designed for the identified region.

In some embodiments, the method further comprises designing the primer for the identified region.

In some embodiments of the method, creating and storing data in the first and second index comprises: for each of the nucleic acid sequences in the first set and the second set, dividing the nucleic acid sequence into a plurality of sub-strings; for each of the plurality of sub-strings, storing a data structure in one of the first index or the second index, wherein: the data structure indicates an identity of the nucleic acid sequence, a permutation of bases forming the sub-string, and a position of the sub-string in the nucleic acid sequence; and the data structure is stored in the first index if the sub-string corresponds to a nucleic acid sequence in the first set, and the data structure is stored in the second index if the sub-string corresponds to a nucleic acid sequence in the second set.

In some embodiments of the method, identifying the region as a region appearing in every nucleic acid sequence in the first set comprises: determining, for a given sub-string of a first nucleic acid sequence of the first set, that a corresponding first data structure stored in the first index indicates a common permutation of bases as a second data structure stored in the first index for a second nucleic acid sequence in the first set.

In some embodiments of the method, identifying the region as a region appearing in every nucleic acid sequence in the first set comprises determining that the second data structure indicates: an identity for the second nucleic acid sequence that matches an identity of a nucleic acid sequence that has been determined to include a previously-matched sub-string, wherein the previously-matched sub-string matches the first nucleic acid sequence at a span occurring immediately before the given sub-string in the first nucleic acid sequence; and a position in the second nucleic acid sequence corresponding to a span occurring immediately after the previously-matched sub-string.

In some embodiments of the method, the determination is performed iteratively with respect to different sub-strings of the first nucleic acid sequence and different data structures in the first index, until a plurality of adjacent sub-strings of the first nucleic acid sequence are determined to occur in a same order in each of the other nucleic acid sequences in the first set, wherein the plurality of adjacent sub-strings of the first nucleic acid sequence together are at least a predefined minimum number of bases in length.

In some embodiments of the method, confirming that the region appears in none of the nucleic acid sequences in the second set comprises: determining, for at least one given sub-string of a first nucleic acid sequence of the first set, whether a third data structure stored in the second index for a nucleic acid sequence in the second set indicates all three of: a common permutation of bases as indicated by the first data structure stored in the first index for the first nucleic acid sequence; an identity for the third nucleic acid sequence that matches an identity of a nucleic acid sequence that has been determined to include a previously-matched sub-string, wherein the previously-matched sub-string matches the first nucleic acid sequence at a span occurring immediately before the given sub-string in the first nucleic acid sequence; and a position in the third nucleic acid sequence corresponding to a span occurring immediately after the previously-matched sub-string.

In some embodiments of the method, the determination is performed iteratively with respect to different sub-strings of the first nucleic acid sequence in order to determine that, for every nucleic acid sequence in the second index, at least one data structure fails at least one of the three conditions for at least one sub-string in the region of the first nucleic acid sequence.

In some embodiments of the method, the plurality of nucleic acid sequences comprises one of DNA, cDNA, RNA, mRNA, PNA, or complete DNA sequences.

In some embodiments, a system for identifying a region for which to design one or more primers for nucleic acid sequences is provided, the system comprising: one or more processors; memory storing one or more programs, the one or more programs configured to be executed by the one or more processors and including instructions to: receive genomic data representing a plurality of nucleic acid sequences; create and store data in a first index representing a first set of the plurality of nucleic acid sequences; create and store data in a second index representing a second set of the plurality of nucleic acid sequences; identify a region for which to design a primer that selects for one or more of the nucleic acid sequences in the first set and that discriminates against one or more of the nucleic acid sequences in the second set, wherein the identifying comprises: identifying, by the first index, the region as a region appearing in every nucleic acid sequence in the first set; and confirming, by the second index, that the region appears in none of the nucleic acid sequences in the second set; and generate and output data representing a primer designed for the identified region.

In some embodiments, a non-transitory computer-readable storage medium storing one or more programs for identifying a region for which to design one or more primers for nucleic acid sequences is provided, the one or more programs configured to be executed by one or more processors and including instructions to: one or more processors; memory storing one or more programs, the one or more programs configured to be executed by the one or more processors and including instructions to: receive genomic data representing a plurality of nucleic acid sequences; create and store data in a first index representing a first set of the plurality of nucleic acid sequences; create and store data in a second index representing a second set of the plurality of nucleic acid sequences; identify a region for which to design a primer that selects for one or more of the nucleic acid sequences in the first set and that discriminates against one or more of the nucleic acid sequences in the second set, wherein the identifying comprises: identifying, by the first index, the region as a region appearing in every nucleic acid sequence in the first set; and confirming, by the second index, that the region appears in none of the nucleic acid sequences in the second set; and generate and output data representing a primer designed for the identified region.

BRIEF DESCRIPTION OF THE DRAWINGS

FIG. 2 is a block diagram of an index of reference permutations of nucleic acid sequence portions. The first segment of the nucleic sequence 206 is SEQ ID NO: 1; the second segment of the nucleic sequence 206 is SEQ ID NO: 2. The sequence at position "0" is SEQ ID NO: 3; the sequence at position "1" is SEQ ID NO: 4; the sequence at position "2" is SEQ ID NO: 5; and the sequence at position "3" is SEQ ID NO: 6. The sequence at position "n" is SEQ ID NO: 1; the sequence at position "n+1" is SEQ ID NO: 7; the sequence at position "n+2" is SEQ ID NO: 8. The sequence at position "$4^{k-4}$" is SEQ ID NO: 9. the sequence at position "$4^{k-3}$" is SEQ ID NO: 10; the sequence at position "$4^{k-2}$" is SEQ ID NO: 11; the sequence at position "$4^{k-1}$" is SEQ ID NO: 12.

DETAILED DESCRIPTION OF THE INVENTION

The following description sets forth exemplary systems, methods, techniques, parameters, and the like. It should be recognized, however, that such description is not intended as a limitation on the scope of the present disclosure but is instead provided as a description of exemplary embodiments.

As described below, the techniques, systems, and methods disclosed herein may enable computationally efficient, fast, accurate, adjustable, and scalable identification of target regions for primer design. The methods may rely on the creation, analysis of, and comparison between two indexes of genomic information, where a first index represents nucleic acid sequences of a subset for which a primer is intended to select, and where a second index represents nucleic acid sequences against which the primer is intended to discriminate. The indexes may be used to quickly, efficiently, and accurately locate all regions of a predefined minimum length that are both conserved (e.g., matching, identical) across all of the nucleic acid sequences in the first index and unique against all nucleic acid sequences in the second index. The resulting regions may be referred to as conserved signature regions, where the term "conserved" may refer to a region or string that appears in all members of one set of nucleic acid sequences, and where the term "signature" may refer to a region that does not appear in any members of a second set of nucleic acid sequences. Conserved-signature regions (which may be both conserved and signature) may be expected to be viable for the design of highly discriminatory primers.

Figure 1:
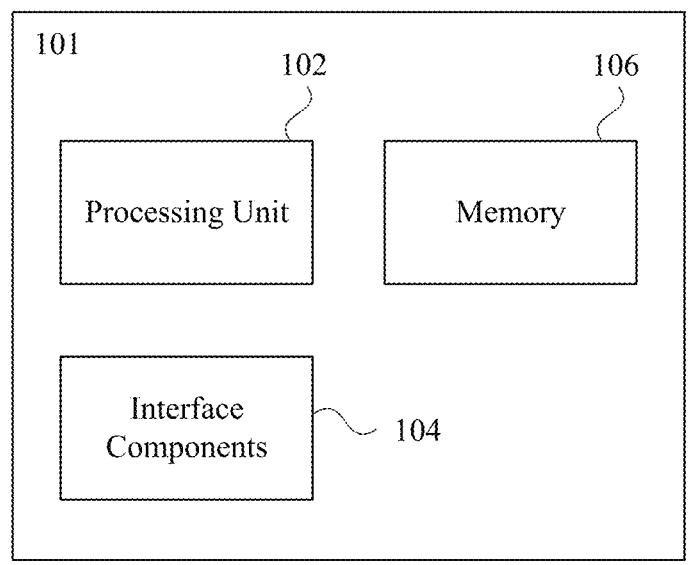
FIG. 1 is a block diagram of a computing system.

Below, FIGS. 1-3 provide a description of exemplary systems and methods for performing the techniques for genomic information compression, transmission, and decompression disclosed herein.

FIG. 1 shows an exemplary system that is configured to perform one or more software processes that, when executed, provide one or more aspects of the disclosed embodiments. FIG. 1 is not intended to be limiting to the disclosed embodiment as the components used to implement the processes and features disclosed herein may vary.

In accordance with certain disclosed embodiments, a computing system 100 may include computer 101. Other components known to one of ordinary skill in the art may be included in system 100 to process, transmit, provide, and receive information consistent with the disclosed embodiments. In some embodiments, the system may contain one or more additional computers or servers and may include one or more communication networks.

Computer 101 may include computer system components, such as one or more servers, desktop computers, workstations, tablets, hand held computing devices, memory devices, and/or internal network(s) connecting the components. In one embodiment, computer 101 may be a server that includes one or more processors, memory devices, and interface components 104. For example, computer 101 may include processing unit 102, memory 106, and interface components 104. Computer 101 may be a single server or may be configured as a distributed computer system including multiple servers or computers that interoperate to perform one or more of the processes and functionalities associated with the disclosed embodiments.

Processing unit 102 may include one or more known processing devices, such as a microprocessor from the Pentium™ family manufactured by Intel™ or the Turion™ family manufactured by AMD™. Processing unit 102 may include a single core or multiple core processor system that provides the ability to perform parallel processes simultaneously. For example, processing unit 102 may include a single core processor that is configured with virtual processing technologies known to those skilled in the art. In certain embodiments, processing unit 102 may use logical processors to simultaneously execute and control multiple processes. The one or more processors in processing unit 102 may implement virtual machine technologies, or other similar known technologies to provide the ability to execute, control, run, manipulate, store, etc. multiple software processes, applications, programs, etc. In another embodiment, processing unit 102 may include a multiple-core processor arrangement (e.g., dual or quad core) that is configured to provide parallel processing functionalities to allow electronic computing system 100 to execute multiple processes simultaneously. One of ordinary skill in the art would understand that other types of processor arrangements, such as those used in Cray supercomputers, could be implemented that provide for the capabilities disclosed herein.

In some embodiments, computer 101 may be a supercomputer, such as the Cray XMT or Cray XMT 2. Supercomputers may include multiple-core processor arrangements paired with a memory that are configured to provide greater parallel processing functionalities relative to consumer-grade desktop computers, laptops, and the like. The Cray XMT, for example, may include 128 TB (terabytes) of memory and processor cores capable of executing up to 8,192 threads in parallel. Similarly, the Cray XMT 2 may include 512 TB of memory and 128 processor cores, with each processor core capable of executing 128 threads, for a total of 16,384 threads.

In some embodiments, computer 101 may be a consumer-grade desktop computer, laptop computer, tablet, cell phone, or the like.

Computer 101 may include one or more storage devices configured to store information used by processing unit 102 (or other components) to perform certain functions related to the disclosed embodiments. In one example, memory 106 may include instructions to enable the one or more processors in processing unit 102 to execute one or more applications, such as server applications, network communication processes, and any other type of application or software known to be available on computer systems. Alternatively, the instructions, application programs, etc. may be stored in an external storage or available from a memory over one or more networks. The one or more storage devices may be a volatile or non-volatile, magnetic, semiconductor, tape, optical, removable, non-removable, or other type of storage device or tangible computer-readable medium.

In some embodiments, memory 106 may include instructions that, when executed by the one or more processors in processing unit 102, perform one or more processes consistent with the functionalities disclosed herein. Methods, systems, and articles of manufacture consistent with disclosed embodiments are not limited to separate programs or computers configured to perform dedicated tasks. For example, computer 101 may include a memory that may include one or more programs to perform one or more functions for creating, transmitting, receiving, and/or decompressing a compressed representation of genomic information, including as described in the disclosed embodiments. Moreover, the one or more processors in processing unit 102 may execute one or more programs located remotely from system 100. For example, system 100 may access one or more remote programs, that, when executed, perform functions related to disclosed embodiments. Memory 106 may include one or more memory devices that store data and instructions used to perform one or more features of the disclosed embodiments. Memory 106 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Computer 101 may also be communicatively connected to one or more memory devices (e.g., databases (not shown)) locally or through one or more computer networks. The remote memory devices may be configured to store information and may be accessed and/or managed by computer 101. By way of example, the remote memory devices may be document management systems, Microsoft SQL databases, SharePoint databases, Oracle™ databases, Sybase™ databases, or other relational databases. Systems and methods of disclosed embodiments, however, are not limited to separate databases or even to the use of a database.

Computer 101 may also include one or more I/O devices that may comprise one or more interfaces for receiving signals or input from input devices and providing signals or output to one or more output devices that allow data to be received and/or transmitted by electronic computing system 100. For example, interface components 104 may provide interfaces to one or more input devices, such as one or more keyboards, mouse devices, and the like, that enable computer 101 to receive data from one or more users. Further, interface components 104 may include components configured to send and receive information between components of computer 101 or external to computer 101.

One or more computer networks communicatively coupled to computer 101 may be any type of network that provides communications, exchanges information, and/or facilitates the exchange of information between computer 101 and other computing systems and devices. In some embodiments, the networks may be the Internet, a Local Area Network, or other suitable connection(s) that enables computers 101 to send and/or receive information between other components of system 100 or outside system 100.

Computer 101 may create, receive, store, and/or provide an index of a nucleic acid sequence or an amino acid sequence. The index may include a plurality of elements, with each element corresponding to a permutation of a nucleic acid sequence or an amino acid sequence (or another type of sequence). Computer 101 may implement the index using a variety of data structures, such as databases, matrices, arrays, linked lists, trees, and the like. The choice of data structures may vary and is not critical to any embodiment. Computer 101 may store the index in memory 106. More specifically, the index may be stored on hard disk; computer 101 may also load the index into RAM for increased performance.

An example nucleic acid sequence is shown in Table 1, below.

TABLE 1

Example Nucleic Acid Sequence
1234568790123456879012345687901234568790

(SEQ ID NO: 13)
ATTGCTTCCATGGGTC

As shown in Table 1, a nucleic acid sequence contains various combinations of the bases adenine, guanine, thymine, and cytosine, represented by the letters "A," "G," "T," and "C," respectively. The numerical digits included in Table 1 enable convenient identification of the positions of the different bases appearing in the sequence. For example, the base adenine appears in positions 1 and 10 of the sequence appearing in Table 1, which is 16 bases in length.

An example amino acid sequence is shown in Table 2, below.

TABLE 2

Example Amino Acid Sequence
1234568790123456879012345687901234568790

(SEQ ID NO: 14)
DVQMIQSPSSLSASLGDIVTMTCQASQGTSINLNWFQQKP

GKAPKLLIYGSSNLEDGVPSRFSGSRYGTDFTLTISSLED

EDLATYFCLQHSYLPYTFGGGTKLEIKR

As shown in Table 2, an amino acid sequence may contain various combinations of the bases, as represented by the one-letter abbreviations for the standard amino acids. The amino acid sequence shown in Table 2 recites amino acids selected from the 22 standard (proteinogenic or natural) amino acids, but sequences comprising nonstandard amino acid sequences may also be used.

FIG. 2 illustrates an index 200 of a nucleic acid sequence, consistent with some embodiments disclosed herein. Although FIG. 2 illustrates use of nucleic acid sequences, one of ordinary skill in the art would understand how such an example would apply to other types of sequences, such as RNA sequences (e.g., involving the bases adenine, guanine, uracil, and cytosine), sequences of artificially synthesized polymers (such as PNA), and amino acid sequences, including standard (proteinogeneic or natural) and non-standard (non-proteinogenic or non-natural) amino acids.

As shown in FIG. 2, index 200 includes a plurality of elements corresponding to various permutations of nucleic acid sequences. In the case of FIG. 2, each permutation is 16 bases in length, resulting in an index with $4^{16}$ or 4,294,967,296 elements (note that each base of a nucleic acid sequence is one of four types). More generally, the size or the number of elements of index 200 is equal to $4^k$, where k is the length, in bases, of each permutation.

As shown to the left of each element in FIG. 2, a given element of the index may be referred to by its position number. For example, as illustrated in FIG. 2, position "0" refers to the element corresponding to the permutation "AAAAAAAAAAAAAAAA (SEQ ID NO: 3)" (which is also indicated by reference number 202a), position "3" refers to the element corresponding to the permutation "AAAAAAAAAAAAAATT (SEQ ID NO: 6)," and position "n" refers to the element corresponding to the permutation "GTAAGATCCGCTACAA (SEQ ID NO: 1)" (which is also indicated by reference number 202 b). Because the index may have up to $4^k$ elements, as described above, the elements may be referenced beginning from position "0" to position "$4^{k-1}$."

In some embodiments, index 200 may contain a number of elements fewer than the number of possible permutations of sequences of a predetermined length. For instance, computer 101 may use statistical and/or probabilistic methods to reduce the number of elements so that only certain nucleic acid sequences (e.g., those most likely to occur) are included in the index. Such an index has the potential advantage of increased computational efficiency and reduction in memory requirements.

Continuing on, reference numbers 202a, 202b, 202c, and 202d of FIG. 2 represent different elements (e.g., elements "0," "n," "n+2," and "$4^{k-1}$" respectively) appearing in index 200. In some embodiments, reference numbers 204a, 204b, and 204c describe additional features of index 200. In particular, these reference numbers indicate position data corresponding to certain elements of the index, e.g., reference numbers 204a and 204b indicate position data stored in element 202b, and reference number 204c indicates position data stored in element 202c. In some embodiments, such as those in which the index includes reference numbers 204 or other position data, the index may provide information about one or more specific nucleic acid sequences; thus, the position data stored in an element may reflect a position or location of the nucleic acid sequence in which the corresponding permutation occurs. For instance, as shown in FIG. 2, reference numbers 204a and 204b indicate that the permutation corresponding to element n of the index, "GTAAGATCCGCTACAA (SEQ ID NO: 1)," appears beginning at positions "0" and "21" of the nucleic acid sequence 206. Similarly, reference number 204c indicates that the permutation corresponding to element n+2 of the index, "GTAAGATCCGCTACTA (SEQ ID NO: 8)," appears beginning at position "44" of the nucleic acid sequence 206.

In some embodiments, as discussed further below, reference numbers for distinct nucleic acid sequences may be loaded into the same index, such that the index may reflect position data for sub-strings of multiple nucleic acid sequences. In some such embodiments, each reference number include both position data indicating the position of the permutation within the nucleic acid sequence as well as metadata identifying the nucleic acid sequence to which the position data corresponds.

The nucleic acid elemental sequences may be received from an underlying nucleic acid sample sequence, which may be much greater in length (e.g., millions or billions of bases).

In some embodiments, and may not contain any location information such as reference numbers 204 and may not contain other information that is specifically related to a particular nucleic acid sequence. That is, in some embodiments, an index may be a generalized index that represents only the elements of the index and corresponding reference numbers 202, such as elements "AAAAAAAAAAAAAAAA (SEQ ID NO: 3)" through "CCCCCCCCCCCCCCCC (SEQ ID NO: 12)" and the corresponding reference numbers 0 through $4^{k-1}$. In some embodiments, such an index may be a blank slate for decoding position data and/or to which position data and/or reference numbers may thereafter be saved (the process of inserting position data corresponding to a nucleic acid sequence into an index may be called "seeding" the index.).

In some embodiments, an index contain an exhaustive listing of every mathematically possible permutation of bases for one or more given element-lengths k, representing every mathematically possible element of the given length (s) and corresponding reference numbers. In some embodiments, an index may contain less than every mathematically possible permutation; for example, an index may contain every practically possible permutation, such as by using probabilistic or historical data to select a subset of permutations that are likely to occur. In some embodiments, an index may contain every practically possible, mathematically possible, or historically known permutation with respect to a certain species or group of species, such that permutations that will likely not be necessary to compress or decompress genomic information for a certain species or group of species may not be included in an index. In some embodiments, an index may not include permutations that are not known to occur in nature.

In some embodiments, the elements of an index may each be 16 bases in length and 128 bits in size, while the reference numbers may each be 8 bits in size. In some embodiments, the elements may be more or less than 16 bases in length and may be more or less than 128 bits in size. In some other embodiments, the elements may be shorter or longer, which will affect the overall size of each index, and will affect the number of elements that are necessary to represent a given sequence of a certain length. For example, in some embodiments, the elements may each be fewer than 16 bases in length, such as 12 or fewer bases in length, or 8 or fewer bases in length. In some embodiments, the elements may each be more than 16 bases in length, such as 20 or more bases in length, 24 or more bases in length, or 32 bases in length. Using bases comprising more or fewer bases affects the overall size of the index by affecting the size of each element and also the number of permutations $4^k$ that may be included in the index. An important consideration in choosing the number of bases in each index may be the overall storage capacity required to store an index comprised of bases of the chosen length; indexes of bases of a greater length may be require greater storage capacity.

In some other embodiments the elements may be comprised of more or less than four unique nucleotides. For example, some elements may contain a fifth wildcard base in addition to the four nucleotides A, T, C, and G. In such embodiments, $5^k$ elements (as opposed to only $4^k$ elements) are needed in order for an index to represent an exhaustive listing of all possible elements of length k. With elements of length 16, this would increase the number of elements from 4,294,967,296 to 152,587,890,625, representing about a 40-fold increase. With approximately 40 times more elements in such an index, approximately 40 times as much memory could be needed to accommodate such an index, and processing times for searching and navigating such an index could also be slowed.

In some embodiments, an index may be provided by way of physical transportation, such as being provided in a hard drive or in any other suitable computer memory. In some embodiments, an index may be provided by way of wired or wireless network communication, such as transmission over a private network or over the internet. In some embodiments, an index may be built on the computer (e.g., computer 101) on which it resides. For example, a program, application, or other computer instructions may be provided to a computer, allowing the computer to construct the index and store it. For example, an algorithm may be provided as part of a computer program that is provided over the internet, and the algorithm may enable a computer to form and store an index.

In some embodiments, more than one index may be provided in the same computer system or at the same location or to the same party. For example, one index containing elements of length 16 may be provided, and another index containing elements of length 12 may be provided. In some embodiments, one index may contain both elements of length 16 and of length 12, or of any two or more element lengths $k_1$, $k_2$, etc. In some embodiments, such an index may be capable of compressing and/or decompressing genomic information with respect to a compression method using elements of length $k_1$, $k_2$, $k_r$, etc., or any combination thereof. In some embodiments, an index may include multiple sets of reference numbers that allow the index to function as if it were an index containing multiple sets of elements of different lengths k. For example, an index containing $4^{16}$ elements of length 16 may contain every mathematically possible permutation of elements with 16 bases where the bases are either A, G, T, or C. That exhaustive set of $4^{16}$ bases may be understood, however, as itself containing the complete set all $4^{12}$ mathematically possible permutations of elements of length 12 where the bases are either A, G, T, or C. By taking the first 12 bases (or any given contiguous portion of length 12) of each of the 16-base elements, for example, the leading 12 bases of $4^{12}$ of the $4^{16}$ bases may account for an exhaustive set of all $4^{12}$ mathematically possible permutations of elements of length 12. Thus, the $4^{12}$ elements that account for the permutations of elements of length 12 may be assigned, in some embodiments, a second reference number that indicates an element's first 12 bases as being a given permutation. In this manner, by adding just $4^{12}$ (under 17 million) reference numerals to an index having $4^{16}$ (over 4 billion) reference numerals and $4^{16}$ elements, the index may serve as two indexes for compressing and/or decompressing genomic information using elements of 16 and/or 12 bases in length.

Indexes of the type described above are described in detail in U.S. patent application Ser. No. 13/904,738, titled "Systems and Methods for SNP Analysis and Genome Sequencing," and in U.S. patent application Ser. No. 14/718,950, titled "Compression and Transmission of Genomic Information," both of which are hereby incorporated by reference in their entirety.

Primer Design Method

Figure 3A:
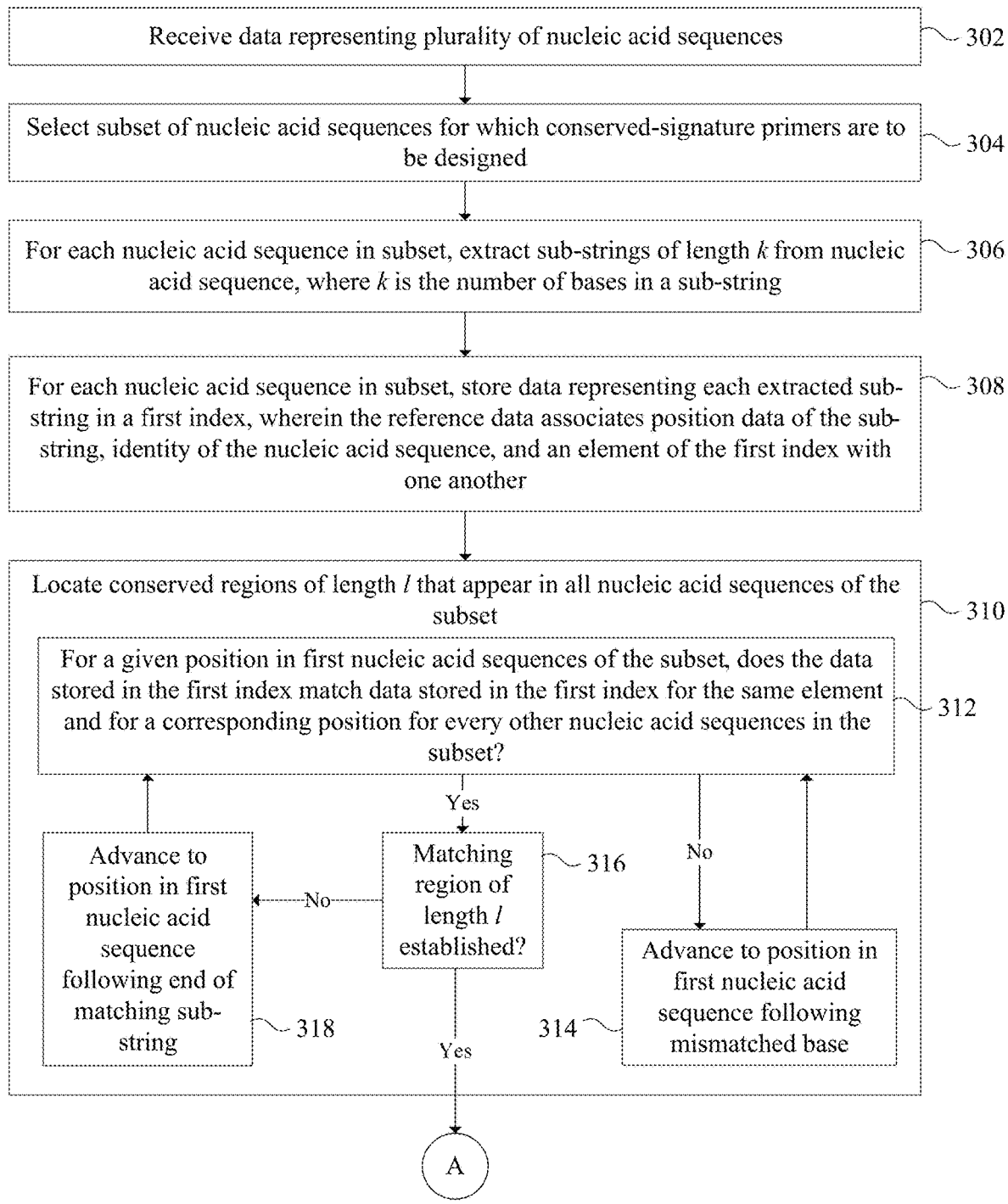
FIGS. 3A and 3B are flow diagrams depicting a method for primer design using indexed genomic information.
Figure 3B:
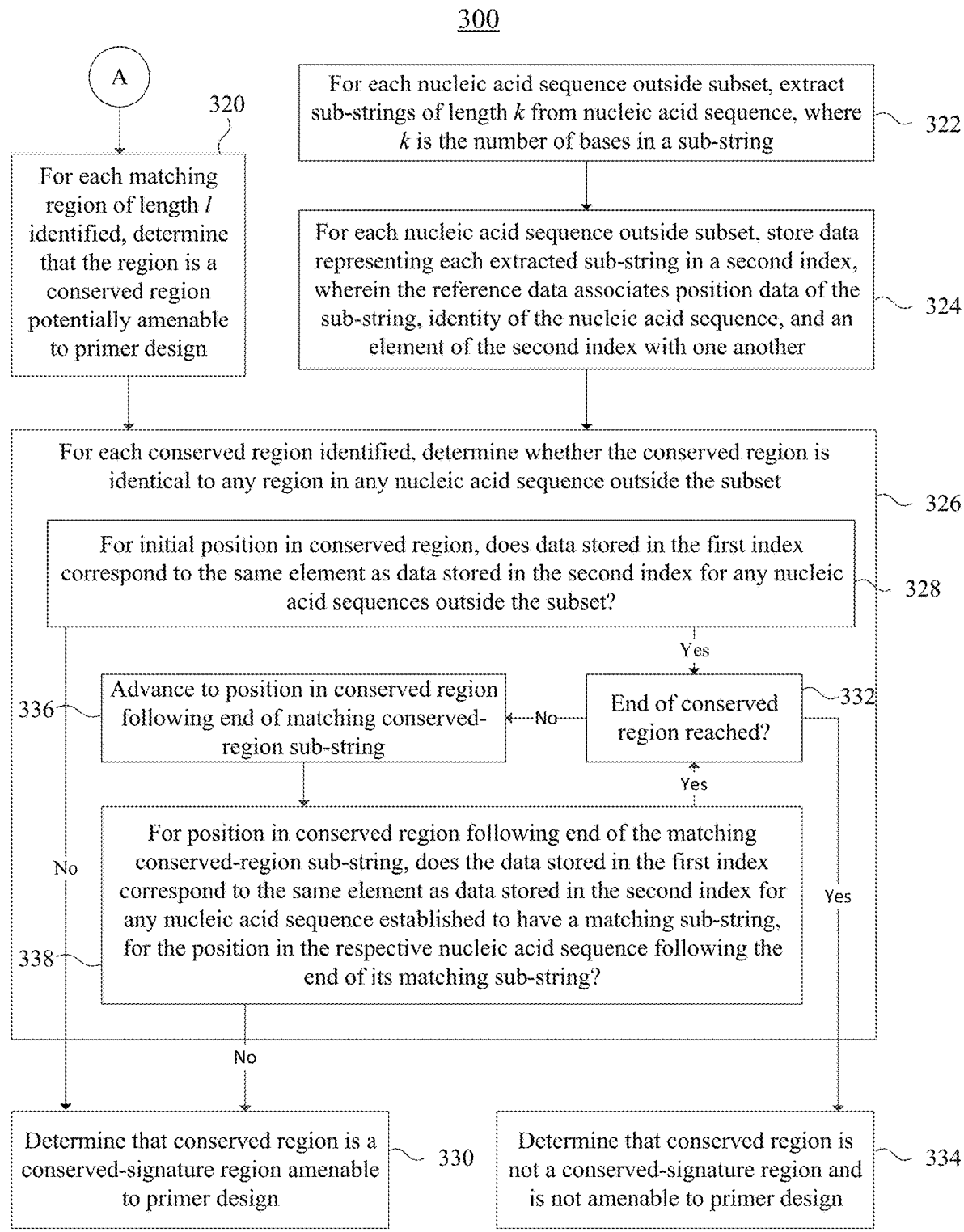

FIGS. 3A and 3B depict a method for primer design using indexed genomic information in accordance with some embodiments. The method 300 may be performed by a system such as the system 100 described above with reference to FIG. 1.

As will be described below, the methods described herein, including exemplary method 300, may achieve computationally efficient, fast, accurate, adjustable, and scalable identification of target regions for primer design. The methods may rely on the creation, analysis of, and comparison between two indexes of genomic information, where a first index represents nucleic acid sequences of a subset for which a primer is intended to select, and where a second index represents nucleic acid sequences against which the primer is intended to discriminate. The first index may be used to quickly, efficiently, and accurately locate all regions of a predefined minimum length that are conserved (e.g., matching, identical) across all of the nucleic acid sequences in the first index; the second index may then be used to quickly, efficiently, and accurately determine which of those conserved regions are unique against all other continuous regions of the same length in any of the nucleic acid sequences in the second index. The resulting regions may be referred to as conserved signature regions, and they may be expected to be highly viable for the design of highly discriminatory primers having minimized false-positive and false-negative selection rates.

At block 302, in some embodiments, data representing a plurality of nucleic acid sequences may be received by a system. In some embodiments, the system receiving the data may be any computer system capable of receiving, storing, and processing data representing a plurality of nucleic acid sequences, such as system 100 of FIG. 1. The data may be received in any suitable manner, including receiving the information over a computerized communication medium (e.g., network communication, communication with physical storage media, manual entry, etc.) and including deriving and/or aligning the information directly (e.g., the input data may be extracted and/or aligned by the same computer that compresses the input data).

The data representing a nucleic acid sequence may be in any suitable and readable format, and may represent any portion of a genomic sequence, including a complete genomic sequence (e.g., Whole Genome Sequencing data, or "WGS" data). The data may be expressed in any suitable language or character encoding scheme, including, for example, ASCII or UTF-8.

In some embodiments, the data may represent a large body of nucleic acid sequences, such as hundreds of thousands or millions of nucleic acid sequences, taken from a database or database of genomic information. In some embodiments, the data may be received from one or more public databases, such as databases accessible via the internet, such as a National Center for Biotechnology Information (NCBI) database; in some embodiments, one or more private databases or sources of genomic information may alternately or additionally be used.

In some embodiments, the data may include metadata associated with one or more of the nucleic acid sequences, and such metadata may identify an organism or organisms associated with a nucleic acid sequence (e.g., the metadata may identify the nucleic acid sequences).

In some embodiments, other metadata included in the data may include one or more parties or organizations associated with the nucleic acid sequences; one or more data sources; location information and/or time information relating to a sample from which a nucleic acid sequence was derived; a type of a sample; a manner in which a sample was collected; a party that collected a sample; a manner in which (and parties by which) a sample was transported; locations and/or routes along which a sample was transported, including times at which the sample was present at various locations; confidentiality metadata indicating a confidentiality level of a sample and/or of an associated party; genomic information that is known or suspected about a sample before sequencing and/or before post-sequencing bioinformatics processing, such as a known or suspected organism, known or suspected serovar, or other known or suspected genomic information; a time at which a sample was located at one or more facilities or locations; personnel that came into contact with a sample at various times; and/or a transportation service associated with a sample.

At block 304, in some embodiments, a subset of nucleic acid sequences for which discriminatory regions targetable for primer design are to be identified may be selected by the system. In some embodiments, the system or a user of the system may select a characteristic, identity, and/or group for which discriminatory assays are needed and for which primers need to be designed. For example, a subset of nucleic acid sequences sharing a taxonomic identification/classification may be selected when a user or system determines that primers need to be designed for a genus, species, or strain of organism(s). In another example, a subset of nucleic acid sequences sharing a phenotypic trait may be selected when a user or system determines that primers need to be designed for the phenotypic trait. In another example, a subset of nucleic acid sequences known to have antibiotic resistance traits may be selected when a user or system determines that primers need to be designed for the antibiotic resistance traits.

Regardless of the nature of the characteristic, identity, and/or group that defined the subset selected, the system may identify members of the subset based on any characteristic of the data and/or metadata received by the system, and may store one or more indications of or copies of the data representing the nucleic acid sequences that constitute the subset.

At block 306, in some embodiments, for each nucleic acid sequence in the subset, sub-strings of length k may be extracted from the nucleic acid sequence, where k is the number of bases in a sub-string. In some embodiments, each nucleic acid sequence may be divided into (L−k+1) sub-strings, where L is the number of bases in the original nucleic acid sequence. In the example of system 100 of FIG. 1, processing unit 102 may process the data in order to divide the nucleic acid sequences in the subset, and data representing the resulting sub-strings may be stored on memory 106.

In some embodiments, this process of dividing a string of genomic data (e.g., a nucleic acid sequence) into a plurality of sub-strings may be referred to as "k-merizing" the string of genomic data, in that each of the sub-strings into which the string is divided may be referred to as a k-mer. In some embodiments, the specific number to which k is set may be used to refer to the k-mer; for example, if k is equal to 16, then the k-mer may be referred to as a 16-mer, and if k is equal to 12, then the k-mer may be referred to as a 12-mer. By selecting a predetermined length k, and dividing an overall string of genomic information into sub-strings of length k by shifting down the string by one base per iteration, the overall string may be k-merized into (L−k+1) sub-strings or k-mers of length k.

In some embodiments, the length k may be set, whether in accordance with user input, automatically by the system, and/or in accordance with specific needs of an application. Generally speaking, shorter lengths for k may, in accordance with the techniques and method steps described below, enable longer processing times and smaller data structures; while longer lengths k may enable shorter processing times and larger data structures.

At block 308, in some embodiments, for each nucleic acid sequence in the subset, data representing each extracted sub-string may be stored in a first index, wherein the reference data associates position data of the sub-string, identity of the nucleic acid sequence, and an element of the first index with one another. In some embodiments, this process may include building and/or seeding a first index with information regarding all of the nucleic acid sequences of the subset.

In some embodiments, the system may start with a first index stored on or otherwise accessible by the system (or the first index may be created/built in accordance with instructions accessible by the system), such as by being stored on memory 106. The first index may include a plurality of elements, where each element represents a permutation of nucleic acid bases of the same length k as the length k of the sub-strings into which the nucleic acid sequences of the subset were divided. In some embodiments, the first index may have any or all of the properties described above with respect to index 200 of FIG. 2.

Initially, the first index may be a "blank-slate" index such as the index described above with reference to FIG. 2, in that it may not contain any location information such as reference numbers 204 and may not contain other information that is specifically related to a particular nucleic acid sequence. In accordance with the technique of block 308, the system may then seed the first index by inserting a plurality of data structures into the first index, wherein each data structure is associated with one of the sub-strings extracted from a nucleic acid sequence of the subset. In some embodiments, the data structures inserted into the first index may share some or all characteristics in common with the reference numbers described above with respect to FIG. 2. In some embodiments, each data structure inserted into the first index may associate three or more pieces of information with one another: (1) the identity of the nucleic acid sequence from which the sub-string was extracted; (2) the position in the nucleic acid sequence to which the sub-string corresponds; and (3) the element/permutation of the first index to which the sub-string corresponds. In some embodiments, the three pieces of information indicated above may be associated with one another by associated data stored in a data structure in the first index.

The data corresponding to the identity of the nucleic acid sequence may comprise any suitable metadata, such as the identification metadata described above.

The data corresponding to the position in the nucleic acid sequence to which the sub-string corresponds may comprise a number indicating a base at which the sub-string begins or ends in the nucleic acid sequence. Thus, for the first sub-string in a nucleic acid sequence, the position data saved to the first index may indicate position 1.

Finally, the data corresponding to the element/permutation of the first index to which the sub-string corresponds may comprise a reference to the element in the first index. In some embodiments, the stored reference comprises a pointer to the corresponding element in the first index (and/or the element may include a pointer to the stored reference). The pointer may, for example, be in the form of a reference number. In some embodiments, the reference may subsequently be used to look up the corresponding element in the first index, and may also be used to look up corresponding elements having the same reference number in other indexes (such as the second index described below). In some embodiments, the reference may comprise an 8-bit data structure, such as a single integer in ASCII or UTF-8. For example, the reference may be any one of the reference numbers 0 through $4^{k-1}$ shown in FIG. 2. In some embodiments, the reference may be a data structure of more than or fewer than 8 bits, for example 16 bits, 32 bits, 64 bits, or 128 bits, and may be stored along with, in association with, and/or with pointers to the data indicating the position and identity information discussed above.

In some embodiments, this process may be conceptualized as storing data representing sub-strings in various different "bins" of the first index, where each bin corresponds to a specific element/permutation of the first index. For each sub-string, an indication of position and an indication of the identity of the overall nucleic acid sequence from which the sub-string was extracted may be inserted into a bin that represents the same sequence of base pairs that constitute the sub-string.

Once all sub-strings for all nucleic acid sequences of the subset are seeded into the first index, the first index may contain multiple data structures representing sub-strings that correspond to the same element, indicating that more than one distinct sub-string extracted from the subset of nucleic acid sequences has the same 16 base pairs in the same order. Reference to this first index may thus facilitate the fast look-up of sub-strings in any of the nucleic acid sequences that have been seeded into the first index.

At block 310, in some embodiments, conserved regions of length l that appear in all nucleic acid sequences of the subset may be located. In some embodiments, once the first index has been created and seeded with data corresponding to the sub-strings extracted from the subset of nucleic acid sequences, the system may then determine which, if any, of the extracted sub-strings are conserved across all of the nucleic acid sequences in the subset. Thus, the system may analyze the data stored in the first index in order to search for identical sub-strings that appear in every nucleic acid sequence in the subset. In some embodiments, the system may search for identical sub-strings that appear in any position of all of the nucleic acid sequences, while in some embodiments a system may search only for identical sub-strings that appear in a consistent, corresponding, or identical position in each of the nucleic acid sequences.

In some embodiments, the length l may be automatically determined by a system and/or may be manually settable and adjustable by a user. In some embodiments, longer lengths l may yield fewer sub-strings that are conserved (e.g., common, identical, matching) across all members of the subset, while they may be more likely to yield conserved sub-strings that are unique as compared to all known nucleic acid sequences outside the subset. In some embodiments, a specific length l, or a length l within a certain range, may be desirable for primer design; for example, lengths l of longer than 25, 50, 75, 100, 125, 150, or 200 base pairs may be desirable, while lengths l of shorter than 250, 225, 200, 175, 150, or 125 base pairs may be desirable.

In some embodiments, this locating process may be carried out in accordance with blocks 312 to 316. As explained below, the system may scan down the length of any one of the nucleic acid sequences of the subset in order to verify that it matches all other nucleic acid sequences in the subset at each sub-string of length k; when a continuous common portion of minimum length l is located across all nucleic acid sequences in the subset, then the system may determine that the portion is a conserved region. As compared to making this comparison on a base by base basis, using the first index to compare on a k-mer by k-mer basis may make this process significantly more fast and efficient. The process is explained further below with respect to blocks 312 to 316.

At block 312, in some embodiments, for a given position in a first nucleic acid sequence of the subset, it may be determined whether the data stored in the first index for that given position of the first nucleic acid sequence matches the data stored in the first index for the same element and for a corresponding position for every other nucleic acid sequence in the subset. Any one of the nucleic acid sequences in the subset may be selected as the first nucleic acid sequence to start the comparison; in some embodiments, the longest nucleic acid sequence of the subset may be selected, the nucleic acid sequence having the most reliable or highest quality data may be selected, or a user may manually choose one of the nucleic acid sequences in the subset to serve as the first nucleic acid sequence.

The system may begin the determination of block 312 by analyzing an initial position of the first nucleic acid sequence by determining whether data stored in the first index for the first nucleic acid sequence matches data stored in the first index for all other nucleic acid sequences in the subset. In order to determine that a region is conserved, it may be required that the portions of the region be located in every one of the nucleic acid sequences and in a corresponding position in each nucleic acid sequence.

In some embodiments, the system may require that position data stored in the first index be matched across all sequences in the index in order for a matching k-mer to successfully be established and for the technique to proceed to block 316. However, matching or identical position data across all sequences in the index may not be required in all embodiments. For example, if all of the sequences in the subset are complete genome WGS data, then conserved regions of sufficient length l may only be found at the same absolute biological position in the genome, and should therefore have identical position data for all complete genome sequences. However, if any of the nucleic acid sequences in the first subset are not a complete genome, and instead represent a portion of the genome starting at a different base than other sequences in the sub-set, then position data seeded into the index for each genome may not be identical for bases that correspond to the same absolute biological position in the genome. For example, position data may be shifted by five bases for a sequence in which the first five bases are missing. Furthermore, in some embodiments, a system may not require that position for conserved regions is common across different nucleic acid sequences at all, such that a primer selecting for any portion of each of the nucleic acid sequences in the subset may be targeted for design, even if the primer selects for identical portions at different positions of different nucleic acid sequences.

In some such embodiments, the system may not require absolute matching of position data across all nucleic acid sequences in the first index. Instead, the system may ensure that position data for all sequences in the subset adequately corresponds across the length of an entire conserved region/ in order to establish that the same continuous identical string of l bases exists in each nucleic acid sequence. Requiring that the portions of the continuous region be located in a "corresponding" position in each nucleic acid sequence may simply require that each nucleic acid sequence has all bases of the continuous portion in the same order with respect to one another, while it may not require that the overall conserved region is located at the same absolute position in each nucleic acid sequence. In some embodiments, ensuring that conditions requiring corresponding positions are satisfied may simply require ensuring that each portion of a conserved region is offset from each other portion of a conserved region by the same number of bases in each nucleic acid sequence. Thus, ensuring that position data corresponds may include ensuring that position data for each k-mer included in a conserved region are set off from one another by the same number of bases across all nucleic acid sequences, even if the absolute position data stored in the first index indicates that the conserved region starts a different number of bases from the beginning of one or more of the nucleic acid sequences.

Alternately, in some embodiments, nucleic acid sequences of different length or starting at different portions in the genome may be accounted for by normalizing the position data for absolute biological position in the genome before storing position data to the index, such as by aligning partial nucleic acid sequences to a complete genome and using a common position convention (e.g., a convention geared to the complete genome) for position data in the first index.

In some other embodiments, however, a system may require that position data (e.g., absolute position data and/or the position of a continuous region in the genome itself) match for each nucleic acid sequence, indicating that the same conserved portion is located at the same absolute biological position of each nucleic acid sequence. For example, requiring that the position be the same at which matching portions are found across the different sequences in the subset may prevent the possibility that a region is selected for primer design where the region may select for multiple different regions in the same genome or set of similar genomes, as this could undermine the efficacy of the assay. Thus, the system may in some embodiments search only for portions that are identical across all nucleic acid sequences at a common position in each of the nucleic acid sequences.

Thus, when checking position data stored in the indexes during the processes described herein, it may be said generally that the system may determine whether the position data for each k-mer meets predefined position criteria, which may vary depending on the application. In some embodiments, meeting predefined position criteria may require, as described above, that the position data indicates a specific absolute position. In some embodiments, meeting predefined position criteria may require, as described above, that the position data indicates a predefined offset number of bases from one or more previously matched k-mers, such that the system may determine that the matching k-mer strings continue to form a continuous conserved portion.

In order to determine that portions of a region are located in every one of the nucleic acid sequences and in a corresponding position in each nucleic acid sequence, the system may first look up the data stored in the first index corresponding to the initial position of the first nucleic acid sequence. The system may check what element of the index is pointed to by that data (or what element of the first index points to it), and the system may look for all other data in the first index that is associated with that data. If the system determines that the first index includes one or more data structures associating that element with each of the other nucleic acid sequences in the subset, and that all of those data structures have corresponding position data, then the system may determine that the initial sub-sequence of length k of the first nucleic acid sequence is also located in each of the other nucleic acid sequences in the subset, and that it is located at a same or corresponding position.

It should be noted that, in some embodiments, whether position data is "corresponding" for multiple different nucleic acid sequences may be defined with respect whether the position data in each nucleic acid sequence bears the same relationship to position data for other data structures corresponding to other sub-strings for the same element. Thus, if a system is searching for a second sub-string located 16 bases further along the nucleic acid sequence from the first matching sub-string, then position data indicating a position 16 bases further along the sequence (regardless of the absolute position in any given nucleic acid sequence) may be said to be corresponding, while position data indicating a position elsewhere in a nucleic acid sequence may be said to be not corresponding. In this way, only matching sub-strings that continue to combine toward establishing a continuous matching region of length l may be returned as matching, while those that are located at another location in a nucleic acid sequence and do not contribute to combining toward establishing a continuous matching region of length l may not be counted.

It should also be noted that, when searching for an initial matching sub-string before any other matching sub-strings have been established, the search for matching sub-strings in the other nucleic acid sequences may be completely independent, such that matching data corresponding to the same element for another nucleic acid sequence may be satisfactory to establish a match, regardless of the position data associated with the other nucleic acid sequences for that element.

If the system fails to meet either of the above conditions with respect to locating data in the first index linking the same element to each of the nucleic acid sequences at matching or corresponding positions of each nucleic acid sequence, then the condition of block 312 may fail, and the system may determine that the sub-string corresponding to the current position of the first nucleic acid sequence is not conserved across all of the nucleic acid sequences. In some embodiments, this negative determination may be attributable to one or more SNPs located in the relevant portion of one or more of the nucleic acid sequences in the subset. In accordance with this negative determination at block 312, the system may proceed to block 314.

At block 314, in some embodiments, if it is determined at block 312 that matching or corresponding data is not stored in the first index for every other nucleic acid sequence in the subset, then the system may advance to a position in the first nucleic acid sequence following a mismatched base, and may then return to block 312 (and to either or both of blocks 314 and 316) for iteration. In some embodiments, when the system identifies which base or bases in the first nucleic acid sequence is not matched by every other nucleic acid sequence in the subset, then the system may advance to the position corresponding to the base immediately following a mismatched base, and may return to block 312 to again begin the process of checking for matching data starting at that position. In some other embodiments, when the system cannot or does not determine which of the specific bases in the first nucleic acid sequence is responsible for the sub-string of k bases being determined to not match every other nucleic acid sequence in the index, the system may simply advance by one base (rather than to a specific base) and may return to block 312 to again begin the process of checking for matching data starting at that position.

Returning to block 312, a positive determination may be made regarding matching or corresponding data being stored in the first index for every one of the nucleic acid sequences. Thus, it may be established that a k-mer of the first nucleic acid sequence matches with a corresponding k-mer of each other nucleic acid sequence, and the system may accordingly determine that it is possible that the k-mer of length k is included in (e.g., is the beginning of) a continuous conserved region of length l. The system may thus need to continue to scan down the length of the first nucleic acid sequence to determine whether a conserved region of length l can in fact be established. Therefore, in accordance with a positive determination that corresponding data is found in the first index for each of the nucleic acid sequences with respect to the given position at block 312, the technique may proceed to block 316.

At block 316, in some embodiments, if it is determined at block 312 that matching data is stored in the first index for every other nucleic acid sequence in the subset, then it may be determined whether a conserved region of length l has been established. In instances in which k=l, for example, establishing one matching k-mer across all nucleic acid sequences in the subset may satisfy the condition of establishing a conserved region of length l across all nucleic acid sequences in the subset. However, in other instances where k<l, merely establishing one matching sub-string of length k may not establish an entire conserved region of length l. Therefore, if all continuously matching portions identified by the system up to and including the most recent matching portion do not establish a portion of length l, then the system may need to continue to scan along the first nucleic acid sequence in order to determine that the next portion or portions continue to match, until a conserved region of length l can be established. Accordingly, the technique may proceed from block 316 to block 318.

At block 318, in some embodiments, if it is determined at block 316 that a conserved region of length l has not been established, the system may advance to the first position in the first nucleic acid sequence following the an of the confirmed matching string. Because it has been established at block 312 that matching data for the given position of the first nucleic acid sequence is located in the first index for all sequences in the first index, then it may be determined that the k-mer of the first nucleic acid sequence corresponding to the given position is also located in each of the other nucleic acid sequences in the first index. Therefore, the system may shift down the first nucleic acid sequence by k bases in order to check whether the k-mer immediately following the established matching k-mer in the first nucleic acid sequence also be established to match the next k bases in each of the other nucleic acid sequences in the subset. In this manner, rather than exhaustively checking every base one at a time, the first index may allow for potentially conserved regions of length l to be established on a k-mer by k-mer basis, which may significantly reduce computational requirements and processing times.

After advancing to a position in the first nucleic acid sequence immediately following the most recently established matching k-mer or k-mers, the technique may then return to block 312 (and to either or both of blocks 314 and 316) for iteration until one or more conserved regions of length l are established.

Returning to block 316, if it is positively determined that all continuously matching portions identified by the system up to and including the most recent matching portion do together establish a continuously matching portion of length l across all of the nucleic acid sequences in the subset, then the technique may proceed to block 320.

At block 320, in some embodiments, for each matching region of length l identified, the system may determine that the region is a conserved region potentially amenable to primer design. The system may determine, for example, that the conserved region is likely to be amenable for design of primers that will successfully select for all nucleic acid sequences in the subset. However, the system may not yet be aware of whether primers designed for this region will be adequately discriminatory against nucleic acid sequences not included in the subset. Thus, determining that the region is conserved may ensure that the primers will not result in false-negative failure to select for sequences in the subset, but it may not ensure that the primers will not result in false-positive selection for sequences not in the subset. Accordingly, the system may proceed from block 320 to determine if the conserved region is adequately discriminatory.

Turning to blocks 322 and 324, the steps described in these two blocks may be performed at any time, and need not necessarily follow block 320. However, in some embodiments, they may precede block 326 as discussed below.

At block 322, in some embodiments, for each nucleic acid sequence outside the subset, the system may extract sub-strings of length k from the nucleic acid sequence, where k is the number of bases in a sub-string. At block 324, in some embodiments, for each nucleic acid sequence outside the subset, the system may store data representing each extracted sub-string in a second index, wherein the reference data associates position data of the sub-string, identity of the nucleic acid sequence, and an element of the second index with one another.

Thus blocks 322 and 324 describe k-merizing a plurality of nucleic acid sequences and building an index based on the extracted k-mers. This process may, in some embodiments, share any or all of the characteristics described above with respect to the k-merization and index creation processes of blocks 306 and 308, except that the processes may be applied to all nucleic acid sequences in the received data that do not fall into the subset (rather than being applied only to those nucleic acid sequences that do fall into the subset). (In some embodiments, rather than applying the techniques of blocks 322 and 324 to all nucleic acid sequences outside the first subset, they may be applied to nucleic acid sequences of any set distinct from the subset used for the first index.) By creating an second index using all nucleic acid sequences outside the first subset, the techniques explained below may be facilitated in order to locate all regions that are (a) conserved among all of the nucleic acid sequences in the first subset and (b) not found in (e.g., discriminatory against) any other known nucleic acid sequence.

In some embodiments, the second index may be created by the same or different computing systems as the first index, and may be stored on the same or different computing systems as the first index. In some embodiments, the first and second index may be stored on the same memory or in the same database, or may be stored in such a manner that one or more processors may operate on both indexes in order to compare the data compared in each index, including as described below.

At block 326, which may follow from blocks 320 and 324, in some embodiments, the system may determine, for each conserved region identified, whether the region is identical to any region in any nucleic acid sequence outside the subset. As described below, this determination may be made by comparing data stored in the first index to data stored in the second index in order to quickly and efficiently determine whether or not the identified conserved region is unique against all nucleic acid sequences outside the subset corresponding to the first index.

At block 328, in some embodiments, the system may determine whether, for the initial position in the conserved region, data stored in the first index corresponds to the same element as data stored in the second index for any nucleic acid sequences outside the subset. Thus, the system may look up, in the first index, the data indicating the initial position of the conserved region. The system may note the element of the first index to which the data for the initial position of the conserved region points, and the system may then check in the second index for any data stored that points to (or is pointed from) the corresponding (e.g., same) element.

If no such data is found in the second index, then the system may determine that the data stored in the first index for the initial position in the conserved region does not correspond to the same element as any data stored in the second index for any of the nucleic acid sequences (and indeed does not correspond to the same element as any of the data stored in the second index at all). In these cases, the technique may proceed to block 330.

At block 330, in some embodiments, the system may determine that the conserved region is a conserved signature region amenable to primer design. Thus, the system may determine, for a conserved region determined to not be identical to any region in any nucleic acid sequence outside the subset, that the conserved region is a discriminatory region targetable for primer design. As discussed above, it may be determined at block 328 that no data in the second index corresponds to the same element as the element corresponding to the first portion of the conserved region, thus indicating that the initial sub-string of length k of the conserved region is not found anywhere in any of the nucleic acid sequences seeded into the second index. That is, the initial sub-string of length k of the conserved region may be determined to be unique against all of the nucleic acid sequences in the second index, therefore establishing that the entire conserved region is necessarily unique against all strings of length l in the nucleic acid sequences in the second index (due at least, but not necessarily exclusively, to the unique sub-string of length k beginning at the initial position of the conserved region). Thus, the system may determine that the conserved region is both (a) conserved among all members of the subset and (b) unique against all members outside the subset, therefore making the region a conserved signature region amenable to primer design for selection of all members in the subset and discrimination against all members outside the subset.

Returning to block 328, the system may determine that, for the initial position in the conserved region, data stored in the first index corresponds to the same element as data stored in the second index for any nucleic acid sequences outside the subset.

While the absence of any data in the second index corresponding to the matching index associated with the initial position of the conserved region may indicate that no sub-string matching the initial sub-string in the conserved region exists anywhere in any nucleic acid sequence outside the subset, the presence of any such data may indicate the opposite. That is, in some embodiments, the presence of any data seeded into the second index at the element corresponding to the relevant element from the first index (e.g., the matching or identical element), may indicate that at least one of the nucleic acid sequences outside the subset contains an identical sub-string to the sub-string defining the first k bases of the conserved region. In these cases, the system may thus determine that the data stored in the first index for the initial position in the conserved region does correspond to the same element as data stored in the second index for one or more of the nucleic acid sequences outside the first subset.

In some embodiments, when the second index contains additional data corresponding to additional nucleic acid sequences against which the system is not checking the conserved region, then the system may perform an additional check to determine whether any of the data pointing to or being pointed from the relevant element in the second index corresponds to a relevant nucleic acid sequence against which the system is comparing the conserved region.

In these cases, because it is determined that the sub-string defining the first k bases on the conserved region matches a sub-string of k bases somewhere in one of the nucleic acid sequences represented in the second index, the system may continue to check the nucleic acid sequences represented in the second index that show a matching sub-string of length k, to determine whether an entire region of length l can be established. This may be achieved, in some embodiments, by the technique shown in blocks 332-338. Thus, in response to determining that the sub-string defining the first k bases on the conserved region matches a sub-string of k bases somewhere in one of the nucleic acid sequences represented in the second index, the technique may proceed to block 332.

At block 332, in some embodiments, the system may determine whether the end of the conserved region has been reached. The system may determine whether the portion(s) of the conserved region that have been established to match a portion of one or more of the nucleic acid sequences in the second index account for the entirety of the conserved region. For example, in embodiments where k=l, this condition may be satisfied after establishing that any one sub-string (e.g., the initial element checked) in the conserved region matches a sub-string in one of the nucleic acid sequences in the second element. If this is the case, then the system may determine that the entire conserved region l matches at least one continuous portion in one of the sub-strings outside the subset and represented by the second index, and may therefore immediately proceed to block 338.

At block 338, in some embodiments, the system may determine that the conserved region is a not a conserved signature region and is not amenable to primer design. Thus, the system may determine, for a conserved region determined to be identical to at least one continuous region in at least one other nucleic acid sequence outside the subset, that the conserved region is not a discriminatory region targetable for primer design. The system may determine that, while the conserved region is consistent among all members of the subset, it is not unique against all members outside the subset. Therefore, primers designed for the conserved but non-discriminatory region may select for nucleic acid sequences not in the subset, therefore making the region non-optimal for primer design for selection of all members in the subset and discriminatory against all members outside the subset.

Returning to block 332, it may instead be determined that the end of the conserved region has not been reached in the comparison of the conserved region against the nucleic acid sequences in the second index. For example, when k<l, mere determination that the first k bases of the conserved region appear in at least one nucleic acid sequence represented by the second index may be insufficient to determine that the entire conserved region l appears in any one of the nucleic acid sequences represented by the second index. Accordingly, the system may need to proceed down the conserved region to check the next portion, and the portion after that, and so on, to determine whether any of the nucleic acid sequences outside the subset indeed include a string that matches the entirety of the conserved region. Thus, the technique may proceed to block 336.

At block 336, in some embodiments, the system may advance to the position in the conserved region following the end of the matching conserved region sub-string. The matching conserved region sub-string may refer to the most recent and/or furthest advanced sub-string that has been determined by the system to match one or more sub-strings in one of the nucleic acid sequences represented by the second index. Thus, following the initial determination at block 328 that the k-mer beginning at the initial position of the conserved region also appears in one or more of the nucleic acid sequences of the subset, the system may advance to the k-mer beginning at the (k+1) position of the conserved region. The technique may then proceed to block 338.

At block 338, in some embodiments, the system may determine, for the position in the conserved region following the end of the matching conserved region sub-string, whether the data stored in the first index corresponds to the same element as data stored in the second index for any nucleic acid sequence established to have a matching sub-string, for the position in the respective nucleic acid sequence following the end of its matching sub-string. That is, after advancing to the position in the conserved region following the end of the most recent sub-string in the conserved region determined to match one or more sub-strings in a nucleic acid sequence of the second index, the system may check where the data corresponding to that position for the conserved region has been seeded into the first index. To do this, the system may look up the data corresponding to the new position in the conserved region, and may check which element in the first index is pointed to. The system may then turn to the second index, and may look up all data that points to (or is pointed to by) the corresponding (e.g., matching) element in the second index. Any data that has been seeded into the second index to correspond to the matching element in the second index may indicate that at least one nucleic acid sequence in the second index contains a sub-string that matches the sub-string of the conserved region that begins at the new position.

However, unlike at block 328, merely establishing that a matching sub-string (e.g., a matching k-mer) exists anywhere in any of the nucleic acid sequences represented by the second index may not be informative of whether any region potentially matching the conserved region exists. Here, since the system has already determined which nucleic acid sequences of the second index have sub-strings for the previously analyzed sub-strings of the conserved region, the system may only be interested in further analysis of the same nucleic acid sequences previously indicated as potentially matching. Furthermore, because a continuous matching region of all l bases in the same order as the conserved region may be required to establish that the conserved region is not unique, the system must also establish that any matching sub-string in the relevant nucleic acid sequence is located at the position of the nucleic acid sequence following the end of the sub-string of the nucleic acid sequence that was most recently established to match a sub-string of the conserved region. Put simply, the system may seek to check whether any of the nucleic acid sequences established as matching an initial portion of the conserved region continue to match the next portions of the conserved region in the next portions of that nucleic acid sequence.

In order to do this, the system may read any data found in the second index associated with the matching element looked up in the first index, and may check whether any of that data (a) corresponds to a nucleic acid sequence that was previously established to match all previously checked portions of the conserved region, and (b) corresponds to the position in the previously matching nucleic acid sequence following its previously matched portion. (In some embodiments, satisfying criteria (b) may be referred to as satisfying position criteria. Generally speaking, satisfying position criteria while checking for uniqueness against the second index may require that a potentially matching portion is determined to appear in the correct spatial/positional relation to all other matching portions of the region. When checking an initial sub-string of a conserved portion against the second index, all matching k-mers indicated in the second index may be determined to satisfy position criteria; thereafter, additional k-mers may be required to be located adjacent to and/or immediately after previously-matched k-mers in the nucleic acid sequence of the second index in order to satisfy position criteria.) In some embodiments, the system may do this by checking whether any data structure stored in association with the relevant index has the same identification metadata as a nucleic acid sequence previously matching all checked portions of the conserved region, and whether the position data associated with that data structure indicates a position immediately following all previously matching portions in the relevant nucleic acid sequence. Thus, if it is established that both conditions are met (e.g., that a data structure in the second index associates the relevant element with a previously matching nucleic acid sequence at the immediate next portion of the nucleic acid sequence), then the system may determine that the conserved region continues to match at least one portion of at least one of the nucleic acid sequences represented by the second index.

In accordance with the determination above (e.g., that the conserved region continues to match at least one portion of at least one of the nucleic acid sequences represented by the second index), the system may revert to block 332 again and determine whether the entire length l of the conserved region has been checked and accounted for by any of the one or more matching nucleic acid sequences in the second index. If, accounting for the sum of all of the contiguous matched sub-strings in any one given nucleic acid sequence, the entire conserved region has been matched (e.g., the end of the conserved region has been reached), then the system may proceed to block 334, as discussed above. If, accounting for the sum of all of the contiguous matched sub-strings in any one given nucleic acid sequence, the entire conserved region has not yet been matched (e.g., the end of the conserved region has not yet been reached), then the technique may return to blocks 336 and 338 by advancing further down the conserved region, and continuing to iterate the process described herein to check whether the potentially matching regions of the nucleic acid sequences continue to match the conserved region.

However, if during any iteration of block 338, it is determined that any of the conditions explained with respect to block 338 are not met for any remaining nucleic acid sequences outside the subset, then the technique may proceed immediately to block 330, as explained above. For example, if, for any element in the first index corresponding to the position in the conserved region currently being checked, the matching element in the second index does not contain a data structure matching both the identity of a previously matched nucleic acid sequence and the next position in that nucleic acid sequence following the insofar matching portion, then the system may immediately determine that the conserved region does not match the nucleic acid sequence at the portion being checked, and that the entire conserved region is therefore not identical to any portion of the nucleic acid sequence. The system may thus determine, if a non-matching element is established for every nucleic acid sequence in the second index, that the conserved region is indeed a conserved signature region amenable to primer design.

In some embodiments, when a system is locating conserved regions of minimum length l, the system may discover a conserved region of length l but may not stop scanning down the first nucleic acid sequence, and may not jump to the end of the conserved region to begin scanning again from that location. Instead, by continuing to scan down the nucleic acid sequence on a base by base or k-mer by k-mer basis, until a non-matching sub-string and/or non-matching base is encountered, the system may establish a conserved region of a length greater than l. In this way, the system may establish a plurality of conserved regions of length l, each largely overlapping and shifted by just one base from one another, each of which may be tested to determine whether it is unique against all nucleic acid sequences not in the subset. Thus, if the first conserved region of length l is determined not to be unique against all nucleic acid sequences outside the subset, then the system may be able to shift down by one base at a time and check whether any of those conserved regions of length l are unique.

In some embodiments, any or all of the techniques of method 300 may be performed in a different order, or may be performed in parallel. For example, in the above description, only portions that are determined to be conserved are checked for uniqueness against all sequences in the second index. However, in other embodiments, both conserved validation (e.g., block 310) and signature validation (e.g., block 326) may be performed in parallel (e.g., simultaneously). For example, system may align all sequences to multiple indexes, and then determine if the sequence aligns perfectly or imperfectly with the index; a perfect alignment to the first index may indicate conserved portions, while an imperfect alignment to the second index may indicate signature portions. In some embodiments, these determinations may be undertaken simultaneously and/or during overlapping time-frames.

Primer Viability Assessment and Assay Validation

Following the location of one or more conserved signature regions for the target subset of nucleic acid sequences, validation of the conserved signature regions for primer design may be performed. For example, one or more tools such as BLAST or Primer3 may be used to validate primer viability and analyze the identified conserved signature regions and to assign one or more scores or rankings to each conserved signature region. Additional information about the identified regions may also be returned by one or more such tools, including information regarding stability of the region (e.g., the presence or absence of any housekeeping genes in the region). In some embodiments, it may be considered preferable to design primers around regions that are known to be stable, so conserved signature regions known to be stable may be scored more highly than conserved signature regions not known to be stable.

In some embodiments, if one or more scores or criteria for primer viability for one or more of the conserved signature regions identified falls below a predefined threshold, then the system may determine that new and/or additional conserved signature regions need to be located. In some such embodiments, method 300 described above may be undertaken once more with a different length l, a different subset of nucleic acid sequences for the first index, and/or a different set of nucleic acid sequences for the second index.

In some embodiments, such as when a conserved signature region is established to be unsatisfactory for primer design, it may become desirable to locate a longer conserved signature region. In these embodiments, regions that are known to be signature (e.g., unique against all nucleic acid sequences outside the subset) may be extended in either direction, and the resulting region will also be guaranteed to be unique against all nucleic acid sequences outside the subset for at least the same reason that the unextended region was. Thus, when extending a known conserved signature region to check for feasibility of primer design across a longer region, it may only be necessary to check whether the extended region is conserved across all nucleic acid sequences in the subset, and it may not be necessary to perform any further signature validation.

In some embodiments, currently existing assays may be validated for their current effectiveness, as the effectiveness of an assay may shift over time given evolution of the target organisms. For example, one or more tools may be used to return metrics regarding the effectiveness of an assay, such as the false-positive rate or the false-negative rate of the assay. In some embodiments, if one or more of the metrics for an existing assay falls below a predefined threshold, then the system may determine that new assays need to be designed, and the system may automatically undertake method 300 in order to identify conserved signature regions or primer design in light of the most complete and up-to-date genomic information available.

In some embodiments, a system for locating regions for primer design may be configured to receive feedback and/or validation from one or more laboratories regarding the feasibility of one or more regions for primer design. In some embodiments, the exhaustive search methods outlined herein may be supplemented by feedback data received from one or more laboratories in order to produce more useful and efficient results. For example, a system may be automatically configured to reject or ignore certain regions that laboratories have indicated in the past are infeasible for primer design while otherwise performing an exhaustive search of all regions of a nucleic acid sequence. The system may be configured to generate and store metadata regarding any feedback received about favorable or unfavorable characteristics of particular regions of nucleic acid sequences for primer design, and may retrieve, account for, and/or present that metadata to a user when locating or outputting conserved signature regions.

Although the description herein uses terms first, second, etc. to describe various elements, these elements should not be limited by the terms. These terms are only used to distinguish one element from another.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

What is claimed is:

1. A method for identifying a target region for which to design one or more primers for nucleic acid sequences, comprising:
at a system comprising one or more processors and memory storing instructions executable by the processor:
receiving genomic data representing a plurality of nucleic acid sequences;
creating and storing data in a first index representing a first set of the plurality of nucleic acid sequences, wherein the first index comprises at least $4^{12}$ elements, wherein each of the $4^{12}$ elements represents a respective permutation of nucleic acid sequences, and wherein the data created and stored in the first index comprises a first plurality of data structures each associated with a respective nucleic acid sequence of the first set;
creating and storing data in a second index representing a second set of the plurality of nucleic acid sequences, wherein the first index comprises at least $4^{12}$ elements, wherein each of the $4^{12}$ elements represents a respective permutation of nucleic acid sequences, and wherein the data created and stored in the second index comprises a second plurality of data structures each associated with a respective nucleic acid sequence of the second set;
identifying a target region for which to design a primer that selects for one or more of the nucleic acid sequences in the first set and that discriminates against one or more of the nucleic acid sequences in the second set, wherein the identifying comprises:
identifying, by the first index, the target region as a conserved region appearing in every nucleic acid sequence in the first set; and
confirming, by the second index, that the conserved region appears in none of the nucleic acid sequences in the second set; and
generating and outputting data representing the identified target region.

2. The method of claim 1, further comprising designing a primer for the identified target region.

3. The method of claim 1, wherein creating and storing data in the first index comprises:
for each of the nucleic acid sequences in the first set, dividing the nucleic acid sequence into a plurality of sub-strings;
for each of the plurality of sub-strings, storing a respective one of the first plurality of data structures in the first index, wherein the respective one of the first plurality of data structures indicates an identity of the nucleic acid sequence, a permutation of bases forming the sub-string, and a position of the sub-string in the nucleic acid sequence.

4. The method of claim 3, wherein identifying the target region as a conserved region appearing in every nucleic acid sequence in the first set comprises:
determining, for a given sub-string of a first nucleic acid sequence of the first set, that a corresponding first data structure stored in the first index indicates a common permutation of bases as a second data structure stored in the first index for a second nucleic acid sequence in the first set.

5. The method of claim 4, wherein identifying the target region as a conserved region appearing in every nucleic acid sequence in the first set comprises determining that the second data structure indicates:
an identity for the second nucleic acid sequence that matches an identity of a nucleic acid sequence that has been determined to include a previously-matched sub-string, wherein the previously-matched sub-string matches the first nucleic acid sequence at a span occurring immediately before the given sub-string in the first nucleic acid sequence; and
a position in the second nucleic acid sequence corresponding to a span occurring immediately after the previously-matched sub-string.

6. The method of claim 4, wherein the determination is performed iteratively with respect to different sub-strings of the first nucleic acid sequence and different data structures in the first index, until a plurality of adjacent sub-strings of the first nucleic acid sequence are determined to occur in a same order in each of the other nucleic acid sequences in the first set,
wherein the plurality of adjacent sub-strings of the first nucleic acid sequence together are at least a predefined minimum number of bases in length.

7. The method of claim 3, wherein confirming that the conserved region appears in none of the nucleic acid sequences in the second set comprises:
determining, for at least one given sub-string of a first nucleic acid sequence of the first set, whether a third data structure stored in the second index for a nucleic acid sequence in the second set indicates all three of:
a common permutation of bases as indicated by the first data structure stored in the first index for the first nucleic acid sequence;
an identity for the third nucleic acid sequence that matches an identity of a nucleic acid sequence that has been determined to include a previously-matched sub-string, wherein the previously-matched sub-string matches the first nucleic acid sequence at a span occurring immediately before the given sub-string in the first nucleic acid sequence; and
a position in the third nucleic acid sequence corresponding to a span occurring immediately after the previously-matched sub-string.

8. The method of claim 7, wherein the determination is performed iteratively with respect to different sub-strings of the first nucleic acid sequence in order to determine that, for every nucleic acid sequence in the second index, at least one data structure fails at least one of the three conditions for at least one sub-string in the conserved region of the first nucleic acid sequence.

9. The method of claim 1, wherein the plurality of nucleic acid sequences comprises one of DNA, cDNA, RNA, mRNA, PNA.

10. The method of claim 1, wherein creating and storing data in the second index comprises:
   for each of the nucleic acid sequences in the second set, dividing the nucleic acid sequence into a plurality of sub-strings;
   for each of the plurality of sub-strings, storing a respective one of the second plurality of data structures in the second index, wherein the respective one of the second plurality of data structures indicates an identity of the nucleic acid sequence, a permutation of bases forming the sub-string, and a position of the sub-string in the nucleic acid sequence.

11. The method of claim 1, wherein the first set of the plurality of nucleic acid sequences comprises one or more complete genomic sequences.

12. The method of claim 1, wherein the second set of the plurality of nucleic acid sequences comprises one or more complete genomic sequences.

13. A system for identifying a target region for which to design one or more primers for nucleic acid sequences, the system comprising:
   one or more processors;
   memory storing one or more programs, the one or more programs configured to be executed by the one or more processors and including instructions to:
      receive genomic data representing a plurality of nucleic acid sequences;
      create and store data in a first index representing a first set of the plurality of nucleic acid sequences, wherein the first index comprises at least $4^{12}$ elements, wherein each of the $4^{12}$ elements represents a respective permutation of nucleic acid sequences, and wherein the data created and stored in the first index comprises a first plurality of data structures each associated with a respective nucleic acid sequence of the first set;
      create and store data in a second index representing a second set of the plurality of nucleic acid sequences, wherein the first index comprises at least $4^{12}$ elements, wherein each of the $4^{12}$ elements represents a respective permutation of nucleic acid sequences, and wherein the data created and stored in the second index comprises a second plurality of data structures each associated with a respective nucleic acid sequence of the second set;
      identify a target region for which to design a primer that selects for one or more of the nucleic acid sequences in the first set and that discriminates against one or more of the nucleic acid sequences in the second set, wherein the identifying comprises:
         identify, by the first index, the target region as a conserved region appearing in every nucleic acid sequence in the first set; and
         confirm, by the second index, that the conserved region appears in none of the nucleic acid sequences in the second set; and
      generate and output data representing the identified target region.

14. A non-transitory computer-readable storage medium storing one or more programs for identifying a target region for which to design one or more primers for nucleic acid sequences, the one or more programs configured to be executed by one or more processors and including instructions to:
   receive genomic data representing a plurality of nucleic acid sequences;
   create and store data in a first index representing a first set of the plurality of nucleic acid sequences, wherein the first index comprises at least $4^{12}$ elements, wherein each of the $4^{12}$ elements represents a respective permutation of nucleic acid sequences, and wherein the data created and stored in the first index comprises a first plurality of data structures each associated with a respective nucleic acid sequence of the first set;
   create and store data in a second index representing a second set of the plurality of nucleic acid sequences, wherein the first index comprises at least $4^{12}$ elements, wherein each of the $4^{12}$ elements represents a respective permutation of nucleic acid sequences, and wherein the data created and stored in the second index comprises a second plurality of data structures each associated with a respective nucleic acid sequence of the second set;
   identify a target region for which to design a primer that selects for one or more of the nucleic acid sequences in the first set and that discriminates against one or more of the nucleic acid sequences in the second set, wherein the identifying comprises:
      identifying, by the first index, the target region as a conserved region appearing in every nucleic acid sequence in the first set; and
      confirming, by the second index, that the conserved region appears in none of the nucleic acid sequences in the second set; and
   generate and output data representing the identified target region.

* * * * *